United States Patent
Braun et al.

(10) Patent No.: US 10,179,185 B2
(45) Date of Patent: Jan. 15, 2019

(54) METHOD FOR PRODUCING WATER-ABSORBING POLYMER PARTICLES

(71) Applicant: BASF SE, Ludwigshafen (DE)

(72) Inventors: Markus Braun, Mannheim (DE); Monica Haag, Ludwigshafen (DE); Stephan Deuerlein, Ludwigshafen (DE); Volker Klock, Ludwigshafen (DE); Roland Krauss, Neustadt (DE)

(73) Assignee: BASF SE, Ludwigshafen (DE)

( * ) Notice: Subject to any disclaimer, the term of this patent is extended or adjusted under 35 U.S.C. 154(b) by 252 days.

(21) Appl. No.: 15/308,383

(22) PCT Filed: May 7, 2015

(86) PCT No.: PCT/EP2015/060088
§ 371 (c)(1),
(2) Date: Nov. 2, 2016

(87) PCT Pub. No.: WO2015/169912
PCT Pub. Date: Nov. 12, 2015

(65) Prior Publication Data
US 2017/0065739 A1 Mar. 9, 2017

(30) Foreign Application Priority Data
May 8, 2014 (EP) .................... 14167499

(51) Int. Cl.
| | |
|---|---|
| *A61L 15/24* | (2006.01) |
| *A61L 15/60* | (2006.01) |
| *C08F 2/00* | (2006.01) |
| *C08F 2/10* | (2006.01) |
| *B01J 20/26* | (2006.01) |
| *B01J 20/28* | (2006.01) |
| *C08F 220/06* | (2006.01) |
| *C08J 3/24* | (2006.01) |

(52) U.S. Cl.
CPC .............. *A61L 15/24* (2013.01); *A61L 15/60* (2013.01); *B01J 20/267* (2013.01); *B01J 20/28011* (2013.01); *C08F 2/001* (2013.01); *C08F 2/10* (2013.01); *C08F 220/06* (2013.01); *C08J 3/245* (2013.01); *C08J 2333/02* (2013.01)

(58) Field of Classification Search
CPC ........ A61L 15/60; C08F 220/06; C08L 33/02; B01J 20/28011; C08J 3/245
See application file for complete search history.

(56) References Cited

U.S. PATENT DOCUMENTS

| | | | | |
|---|---|---|---|---|
| 5,275,773 | A | * | 1/1994 | Irie ........................ C08J 3/12 264/141 |
| 2008/0004408 | A1 | | 1/2008 | Stueven et al. |
| 2011/0015362 | A1 | | 1/2011 | Weismantel et al. |
| 2012/0071613 | A1 | | 3/2012 | Stueven et al. |

FOREIGN PATENT DOCUMENTS

| | | |
|---|---|---|
| BE | 1020479 A5 | 11/2013 |
| EP | 0 497 623 A2 | 8/1992 |
| WO | WO-01/038402 A1 | 5/2001 |
| WO | WO-2003/22896 A1 | 3/2003 |
| WO | WO-2003/051415 A1 | 6/2003 |
| WO | WO-2005/097313 A1 | 10/2005 |
| WO | WO-2006/034806 A1 | 4/2006 |
| WO | WO-2006/034853 A1 | 4/2006 |
| WO | WO-2009/115472 A1 | 9/2009 |
| WO | WO-2012/107432 A1 | 8/2012 |
| WO | WO-2014/118024 A1 | 8/2014 |

OTHER PUBLICATIONS

Buchholz, et al., eds., "Modern Superabsorbent Polymer Technology," Wiley-VCH, NY, NY (1998), pp. 71-103.
International Search Report for Patent Application No. PCT/EP2015/060088, dated Aug. 4, 2015.

* cited by examiner

*Primary Examiner* — Mark S Kaucher
(74) *Attorney, Agent, or Firm* — Marshall, Gerstein & Borun LLP

(57) ABSTRACT

A process for producing water-absorbing polymer particles is provided, comprising a) a polymerization step in which an aqueous monomer solution comprising at least one ethylenically unsaturated monomer M which bears acid groups and may have been at least partly neutralized and at least one crosslinker is polymerized to obtain an aqueous polymer gel; b) a pelletization step in which the aqueous polymer gel having a solids content of 35 to 70% by weight and a temperature of 75 to 125° C. is forced from a high-pressure zone through a die plate into a low-pressure zone and pellets are obtained, the pressure differential between the high-pressure zone and the low-pressure zone being 4 to less than 14 bar and the orifice ratio of the die plate being 30 to 80%; c) a drying step in which the pellets are dried to a moisture content of less than 10% by weight; d) a grinding step and a classifying step to obtain water-absorbing polymer particles; and e) surface crosslinking of the water-absorbing polymer particles. The water-absorbing polymer particles have a high swell rate and a high retention capacity combined with a favorable ratio of permeability of the swollen gel bed SFC to centrifuge retention capacity CRC.

11 Claims, No Drawings

METHOD FOR PRODUCING WATER-ABSORBING POLYMER PARTICLES

CROSS-REFERENCE TO RELATED APPLICATIONS

This is the U.S. national phase of International Patent Application No. PCT/EP2015/060088, filed May 7, 2015, which claims the benefit of European Patent Application No. 14167499.4, filed May 8, 2014.

DESCRIPTION

The present invention relates to a process for producing water-absorbing polymer particles having a high swell rate and a high retention capacity combined with a simultaneously favorable ratio of permeability of the swollen gel bed to retention capacity. The process comprises the polymerization of an aqueous monomer solution, a pelletization step, a drying step, a grinding and classifying step and a surface crosslinking operation. The invention also relates to the water-absorbing polymer particles obtainable by the process.

Water-absorbing polymer particles are used to produce diapers, tampons, sanitary napkins and other hygiene articles, but also as water-retaining agents in market gardening. The water-absorbing polymer particles are also referred to as superabsorbents.

The production of water-absorbing polymer particles is described in the monograph "Modern Superabsorbent Polymer Technology", F. L. Buchholz and A. T. Graham, Wiley-VCH, 1998, pages 71 to 103.

The polymer chains of the water-absorbing polymer particles are crosslinked with one another. One effect of this is that the polymer particles are water-insoluble. The properties of the water-absorbing polymer particles can be adjusted via the amount of crosslinker used. As the amount of crosslinker rises, the centrifuge retention capacity (CRC) falls and the absorption under load (AUL) passes through a maximum.

The current trend in diaper construction is to produce thinner constructions having a reduced cellulose fiber content and increased superabsorbent content. The advantage of thinner constructions is manifested not just in improved wearer comfort but also in reduced packaging and storage costs. With the trend toward ever thinner diaper constructions, the profile of requirements on the superabsorbents has changed significantly. What is now of crucial significance is the ability of the hydrogel to conduct liquid (permeability) and distribute it. Because of the higher loading of the hygiene article (amount of superabsorbent per unit area), the polymer in the swollen state must not form a barrier layer for subsequent liquid (gel blocking). Only when the product has good transport properties can the retention capacity of the overall hygiene article be optimally utilized.

As well as the permeability of the superabsorbents (reported in the form of the saline flow conductivity, SFC) and the absorption capacity under load, the absorption rate of the superabsorbent particles (reported in the amount of liquid absorbed per gram of superabsorbent per second, i.e. free swell rate, FSR) in particular is also a crucial criterion which enables conclusions as to whether an absorptive core comprising this superabsorbent in high concentration is able to rapidly absorb these on first contact with liquids (called "acquisition"). In the case of absorbent cores having a high superabsorbent content, this acquisition depends upon factors including the absorption rate of the superabsorbent material.

To improve the use properties, for example permeability in the swollen gel bed in the diaper and absorption under load, water-absorbing polymer particles are generally surface crosslinked. This increases the level of crosslinking of the particle surface, and in this way it is possible to at least partly decouple absorption under load and retention capacity. Crosslinkers suitable for surface crosslinking are compounds which can form covalent bonds to at least two carboxylate groups of the water-absorbing polymer particles.

To increase the swell rate, it has been proposed that a microporous structure be imparted to the water-absorbing polymer particles, which is possible, for example, through the additional use of blowing agents in the polymerization. To date, the increase in the swell rate, however, has always led to a lowering of the retention capacity with comparable permeability of the swollen gel bed, or to a lowering of the permeability of the swollen gel bed with comparable retention capacity. A suitable measure of the quality of a superabsorbent in hygiene articles having an elevated superabsorbent content is the quotient of the permeability of the swollen gel bed to the retention capacity. If the quotient does not exceed a particular value, sufficiently high retention capacities are achieved for a given permeability.

The production of water-absorbing polymer particles in a polymerization reactor with at least two axially parallel rotating shafts (kneaders) is described, for example, in WO 01/038402 A1, WO 03/022896 A1, WO 03/051415 A1, WO 2006/034806 A1, WO 2006/034853 A1 and WO 2009/115472 A1.

The extrusion of the polymer gels which form in the polymerization is described in EP 0 497 623 A2. This involves forcing a crosslinked aqueous polymer gel through a die plate at elevated temperature, and drying and grinding it. The water-absorbing polymer particles thus obtained have a low proportion of extractable polymers and an improved absorption ratio.

WO 2005/097313 A1 discloses a process for producing water-absorbing polymer particles, in which an aqueous polymer gel is comminuted and forced through die plates having a hole diameter of 0.3 to 6.4 mm by means of an extruder, dried and surface crosslinked, which gives polymer particles having a high CRC, SFC and FSR. The products obtained have a high SFC/CRC quotient.

The prior application PCT/EP 2014/050980 discloses a process for producing water-absorbing polymer particles by polymerization, drying, grinding and classification of the resulting polymer gel and surface crosslinking. The aqueous polymer gel is extruded prior to drying. The most preferred orifice ratio is 10 to 20%.

It was an object of the present invention to provide a process for producing water-absorbing polymer particles having a high swell rate and high retention capacity combined with a favorable ratio of permeability of the swollen gel bed SFC to centrifuge retention capacity CRC.

The object was achieved by a process for producing water-absorbing polymer particles, comprising a) a polymerization step in which at least one ethylenically unsaturated monomer M which bears acid groups and may have been at least partly neutralized and at least one crosslinker are polymerized in aqueous solution to obtain an aqueous polymer gel, b) a pelletization step in which the aqueous polymer gel having a solids content of 40 to 80% by weight and a temperature of 75 to 125° C. is forced from a high-pressure zone through a die plate into a low-pressure zone and pellets are obtained, the pressure differential between the high-pressure zone and the low-pressure zone being 4 to 14 bar and the orifice ratio of the die plate being 30 to 80%; and c) a drying step in which the pellets are dried to a moisture content of less than 10% by weight;
d) a grinding step and a classifying step; and
e) surface crosslinking.

The present invention is based on the finding that the properties of water-absorbing polymer particles can be improved when the crosslinked polymer gel produced by polymerization is subjected to a pelletization step in which the polymer is forced through a die plate under controlled conditions. The shear forces that occur lead to roughening of the surface of the extrudates that pass through a die plate, which crumble to form pellets. Because of the elevated homogeneity thereof, the pellets can be dried better compared to compact forms of the polymer gel, for example blocks or extrudates.

In addition, a second effect is thought to occur. The pressure drop and the high temperatures at the outlet from the die plate cause water to evaporate spontaneously out of the aqueous polymer gel. Too few channels are present in the polymer gel to lead off the entirety of the gas. Macropores are therefore formed, which lead to an increase in the surface area of the polymer particles and better flow conduction. Overall, the polymer particles after the surface crosslinking therefore have a high free swell rate (FSR) and a high centrifuge retention capacity (CRC).

The process comprises a polymerization step a) in which at least one ethylenically unsaturated monomer M which bears acid groups and may have been at least partly neutralized and at least one crosslinker are polymerized in aqueous solution to obtain an aqueous polymer gel.

The monomers M are preferably water-soluble, i.e. the solubility in water at 23° C. is typically at least 1 g/100 g of water, preferably at least 5 g/100 g of water, more preferably at least 25 g/100 g of water and most preferably at least 35 g/100 g of water.

Suitable monomers M are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers M are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers M. Suitable purification processes are described, for example, in WO 02/055469 A1, WO 03/078378 A1 and WO 2004/035514 A1. A suitable monomer M is, for example, an acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers M is preferably at least 50 mol %, more preferably at least 90 mol % and most preferably at least 95 mol %.

The acid groups of the resulting polymer gels have typically been partly neutralized. Neutralization is preferably carried out at the monomer stage. This is typically accomplished by mixing in the neutralizing agent as an aqueous solution or preferably also as a solid. The degree of neutralization is preferably from 25 to 85 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and mixtures thereof.

The monomers M typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer M. For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers are compounds having at least two groups suitable for crosslinking. Such groups are, for example, ethylenically unsaturated groups which can be polymerized free-radically into the polymer chain, and functional groups which can form covalent bonds with the acid groups of the monomer M. In addition, polyvalent metal salts which can form coordinate bonds with at least two acid groups of the monomer M are also suitable as crosslinkers.

Crosslinkers are preferably compounds having at least two polymerizable groups which can be polymerized free-radically into the polymer network. Suitable crosslinkers are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 03/104299 A1, WO 03/104300 A1, WO 03/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 02/032962 A2.

Preferred crosslinkers are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers are the polyethoxylated and/or -propoxylated glycerols which have been esterified with acrylic acid or methacrylic acid to give di- or triacrylates, as described, for example, in WO 03/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker is preferably 0.20 to 1.5% by weight and more preferably 0.30 to 1.0% by weight, based in each case on unneutralized monomer M. As the crosslinker content rises, the centrifuge retention capacity (CRC) falls and the absorption under a load of 49.2 g/cm² ($AUL_{0.7psi}$) passes through a maximum.

As the amount of crosslinker falls, the proportion of extractable polymers (extractables) rises. A high proportion of extractable polymers causes, among other effects, a low absorption under a load of 49.2 g/cm² $AUL_{0.7psi}$ and a tacky feel. A favorable maximum ratio of centrifuge retention capacity CRC to extractable polymers therefore points to positive material properties. The CRC/extractables ratio is determined after the pellets have been dried and is preferably at least 2.5.

The monomer solution may comprise an ethylenically unsaturated monomer $M_{co}$ copolymerizable with the monomers M. $M_{co}$ is selected, for example, from acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The monomer solution may comprise one or more water-soluble polymers. Water-soluble polymers used may be polyvinyl alcohol, polyvinylpyrrolidone, starch, starch derivatives, modified cellulose, such as methyl cellulose or hydroxyethyl cellulose, gelatin, polyglycols or polyacrylic acids, preferably starch, starch derivatives and modified cellulose.

An aqueous monomer solution is used. The water content of the monomer solution is preferably from 40 to 75% by weight, more preferably 45 to 70% by weight, most preferably 50 to 65% by weight. It is also possible to use monomer suspensions, i.e. monomer solutions with excess monomer M, for example sodium acrylate. As the water content rises, the energy expenditure in the subsequent drying rises and, as the water content falls, the heat of polymerization can only be removed inadequately.

Initiators used may be all compounds which generate free radicals under the polymerization conditions, for example thermal initiators, redox initiators or photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

In a preferred embodiment of the present invention, the polymerization is performed in the presence of an inert gas and under elevated pressure.

Suitable inert gases are nitrogen, carbon dioxide, steam and argon. The polymerization reaction is inhibited by oxygen. Therefore, the inert gas should comprise preferably less than 0.001% by volume, more preferably less than 0.0005% by volume and most preferably less than 0.0002% by volume of oxygen. Advantageously, the inert gas flows continuously through the polymerization reactor. The inert gas volume flow rate is preferably from 0.001 to 5 m³/h per m³ of reactor volume, more preferably from 0.01 to 2 m³/h per m³ of reactor volume and most preferably from 0.2 to 1 m³/h per m³ of reactor volume.

The inert gas used is preferably nitrogen, more preferably in technical grade quality. Technical grade nitrogen comprises typically at least 99.8% by volume of nitrogen and less than 0.0005% by volume of oxygen.

The gauge pressure in the polymerization reactor is preferably 1 to 500 mbar, more preferably 5 to 100 mbar, most preferably 10 to 30 mbar.

The polymerization reactors usable in the process according to the invention preferably have at least two axially parallel rotating shafts, typically with several kneading and transport elements present on the shafts.

Polymerization reactors usable in the process according to the invention are available, for example, from List AG (Arisdorf; Switzerland) and are described in CH 664 704 A5, EP 0 517 068 A1, WO 97/12666 A1, DE 21 23 956 A1, EP 0 603 525 A1, DE 195 36 944 A1 and DE 41 18 884 A1.

Such polymerization reactors having at least two shafts achieve, by virtue of the arrangement of the kneading and transport elements, a high level of self-cleaning, which is an important requirement for a continuous polymerization. The two shafts preferably rotate counter to one another.

On the stirrer shaft, the disk segments are arranged in the manner of a propeller. Suitable kneading and transport elements are, for example, close-clearance mixing bars and L- or U-shaped attachments.

It is possible to mix recycled polymer particles having a particle size smaller than a preset lower limit ("fines") which have been removed in later process steps and/or originate from other production lines into the aqueous monomer solution and/or the polymerizing aqueous monomer solution in the polymerization reactor and/or into the aqueous polymer gel. The fines can be moistened with water and/or aqueous surfactant before or during the recycling. The addition of fines increases the solids content of the aqueous polymer gel.

If a kneading reactor is used for polymerization, the fines are preferably added during the last third of the polymerization.

If the fines are added at a very early stage, for example actually to the monomer solution, this lowers the centrifuge retention capacity CRC of the resulting water-absorbing polymer particles. However, this can be compensated for, for example, by adjusting the amount of crosslinker used.

In the pelletization step b), the polymer gel is forced through the holes of a die plate. The hole orifices of the die plate are essentially unrestricted in terms of their shape and may, for example, be circular, rectangular, triangular, hexagonal or star-shaped. The hole orifices of the die plate are preferably circular. The diameter of the holes is preferably in the range from 2 to 20 mm, more preferably 4 to 15 mm, most preferably 6 to 10 mm. In the case of noncircular orifices, the hole diameter is defined as the area-based equivalent diameter, i.e. as the diameter of a circle of the same cross-sectional area.

The orifice ratio is defined as the ratio of the open area (sum of the hole areas) of the die plate to the maximum utilizable area of the die plate. The orifice ratio is in the range from 30 to 80%, preferably 40 to 70%, more preferably 50 to 70%.

The length of the holes in the die plate is in the range from preferably 15 to 45 mm, more preferably 25 to 40 mm. If the holes are drillholes in the die plate, the thickness of the die plate corresponds to the length of the holes. The orifices may also be implemented in the form of tubular inserts in the die plate, which may project beyond the die plate. In this case, the hole length corresponds to the length of the inserts.

The pressure differential between the high-pressure zone and the low-pressure zone is within the range from 4 to less than 14 bar, preferably 5 to 13 bar. A lower pressure differential than that specified leads to an undesirably low throughput of the polymer gel through the die plate. Moreover, only an insufficient improvement in the swell rate is achieved. A higher pressure differential than that specified leads to damage to the internal structure of the polymer gel, which can lead to an increase in the content of extractable polymers and an impairment of the retention capacity.

Preferably, the pelletization step b) is conducted in an extruder comprising an elongated extruder housing, an outlet orifice provided with the die plate and at least one screw shaft which rotates within the extruder housing and which conveys the polymer gel in the direction of the outlet orifice while generating a backpressure. In general, the polymer gel is extruded from the high pressure in the interior of the extruder through the die plate to the environment, i.e. the pressure in the low-pressure zone corresponds to the ambient pressure. In order to prevent excessive cooling or heating of the polymer gel during the extrusion, the extruder is preferably trace-heated as required, more preferably with steam, or trace-cooled. The process can be conducted either continuously or batchwise.

It is possible to incorporate recycled fines into the polymer gel in the extruder.

The polymer gel undergoes a mechanical energy input in the extrusion step, particularly through the action of the rotating screw shaft(s). Excessively high energy inputs in the pelletization step b) lead to damage to the internal structure of the polymer gel, which in turn causes worsening of the free swell rate (FSR) and the centrifuge retention capacity (CRC). Excessively high energy inputs should therefore be avoided.

The energy input can be influenced, for example, via the ratio of internal length to internal diameter of the extruder (L/D). The ratio of internal length to internal diameter of the extruder is preferably 1 to 6, more preferably 2 to 5.5, most preferably 3 to 5.

The specific mechanical energy (SME) introduced in the course of extrusion is preferably from 2 to 60 kWh/t, more preferably from 5 to 50 kWh/t and most preferably from 10 to 40 kWh/t. The specific mechanical energy (SME) is the motor output of the extruder in kW divided by the throughput of polymer gel in t/h. This avoids damage to the polymer gel in the course of extrusion.

During the pelletization step b), the polymer gel has a temperature within the range from preferably 75 to 125° C., more preferably 80 to 120° C., most preferably 90 to 105° C.

The solids content SC of the polymer gel before it passes through the die plate is 35 to 70% by weight, preferably 40 to 60% by weight. Since, as explained, the pelletization step b) is associated with the evaporation of water, the solids content of the polymer gel generally rises during the pelletization step b). The ratio of the solids content of the polymer gel after it passes through the die plate to the solids content of the polymer gel before it passes through the die plate ($SC_{post-extr}/SC_{pre-extr}$) is, for example, at least 1.01 or at least 1.05 or at least 1.08.

The pellets obtained in the pelletization step b) are dried. The pellets can be dried by means of any apparatus suitable for that purpose, preferably by means of a belt drier. This involves passing the pellets through one or more drying chambers on a horizontal, perforated drying belt. However, a fluidized bed drier or a paddle drier may optionally also be used for drying purposes. The drying is performed until the residual moisture content is less than 10% by weight, for example 1 to less than 10% by weight, preferably 1.5 to 8% by weight. The residual moisture content is determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and undesirably large amounts of polymer particles having particle sizes of less than 150 μm ("fines") arise in the subsequent comminution steps.

The dried pellets are subsequently ground and classified. Grinding can typically be accomplished using one-stage or multistage roll mills, preferably two or three-stage roll mills, pinned disk mills, hammer mills or vibratory mills. The classification comprises at least two screens, in which case additional screens can be used as what are called guard screens, in order to avoid blockage of the screen pores. The classification removes both polymer particles having a particle size greater than a preset upper limit ("coarse particles") and polymer particles having a particle size smaller than a preset lower limit ("fines"). A typical upper limit is, for example, 710 μm, a typical lower limit 150 μm.

Coarse particles lower the swell rate. Therefore, the proportion of coarse particles should be low. Coarse particles are therefore typically removed and recycled into the grinding of the dried polymer gel.

Fines lower the permeability of the swollen gel bed (SFC). Therefore, the proportion of fines should be low.

The fines are therefore typically removed and recycled into the process, as explained above. It is also possible to remove fines in later process steps, for example after the surface crosslinking or another coating step. In this case, the recycled fines are surface crosslinked or coated in another way, for example with fumed silica.

The mean particle size of the polymer particles removed as the product fraction is preferably at least 200 μm, more preferably from 250 to 600 μm, most preferably from 300 to 500 μm. The mean particle size of the product fraction may be determined by means of EDANA recommended test method No. WSP 220.2-05 "Particle Size Distribution", where the proportions by mass of the screen fractions are plotted in cumulated form and the mean particle size is determined graphically. The mean particle size here is the value of the hypothetical equivalent mesh size at which 50% by weight pass through the screen and 50% by weight remain on the screen. It is possible to determine the mean particle size practically by a screen analysis, for example by means of the set of screens used in the examples below. The median particle diameter is the $d_{50}$ of the cumulative particle size distribution.

The proportion of particles having a particle size of at most 710 μm is preferably at least 90% by weight, more preferably at least 95% by weight, most preferably at least 98% by weight.

The proportion of particles having a particle size of greater than 150 μm is preferably at least 90% by weight, more preferably at least 95% by weight, most preferably at least 98% by weight.

The proportion of particles having a particle size of 300 to 600 μm is preferably at least 60% by weight, more preferably at least 65% by weight and most preferably at least 70% by weight.

To further improve the properties, the polymer particles are surface crosslinked. Suitable surface crosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Further suitable surface crosslinkers are cyclic carbonates described in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and derivatives thereof in WO 03/031482 A1.

Preferred surface crosslinkers are ethylene carbonate, ethylene glycol diglycidyl ether, reaction products of polyamides with epichlorohydrin and mixtures of propylene glycol and 1,4-butanediol.

Very particularly preferred surface crosslinkers are 2-hydroxyethyl-2-oxazolidinone, 2-oxazolidinone and 1,3-propanediol.

In addition, it is also possible to use surface crosslinkers which comprise additional polymerizable ethylenically unsaturated groups, as described in DE 37 13 601 A1.

The amount of surface crosslinker is preferably 0.001 to 2% by weight, more preferably 0.02 to 1% by weight, most preferably 0.05 to 0.2% by weight, based in each case on the polymer particles.

In a preferred embodiment of the present invention, polyvalent cations are applied to the particle surface in addition to the surface crosslinkers before, during or after the surface crosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are hydroxide, chloride, bromide, sulfate, hydrogensulfate, carbonate, hydrogencarbonate, nitrate, phosphate, hydrogenphosphate, dihydrogenphosphate and carboxylate, such as acetate, citrate and lactate. Salts with different counterions are also possible, for example basic aluminum salts such as aluminum monoacetate or aluminum monolactate. Aluminum sulfate, aluminum monoacetate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight, more preferably 0.01 to 0.8% by weight, based in each case on the polymer particles.

The surface crosslinking is typically performed in such a way that a solution of the surface crosslinker is applied to, for example sprayed onto, the dried polymer particles. After the application, the polymer particles wetted with surface crosslinker are subjected to a thermal aftertreatment. This involves surface crosslinking and drying the polymer particles, and the surface crosslinking reaction can take place either before or during the drying.

The spray application of a solution of the surface crosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface crosslinker solution in a fluidized bed.

The surface crosslinkers are typically used in the form of an aqueous solution. The penetration depth of the surface crosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The surface crosslinking is preferably performed in contact driers, more preferably shovel driers, most preferably disk driers. Suitable driers are, for example, Hosokawa Bepex® Horizontal Paddle Dryers (Hosokawa Micron GmbH; Leingarten; Germany), Hosokawa Bepex® Disc Dryers (Hosokawa Micron GmbH; Leingarten; Germany), Holo-Flite® driers (Metso Minerals Industries Inc.; Danville; USA) and Nara Paddle Dryers (NARA Machinery Europe; Frechen; Germany). Moreover, fluidized bed driers may also be used.

The surface crosslinking can be effected in the mixer itself, by heating the jacket or blowing in warm air. Equally suitable is a downstream drier, for example a shelf drier, a rotary tube oven or a heatable screw. It is particularly advantageous to effect mixing and drying in a fluidized bed drier.

Preferred reaction temperatures are in the range of 100 to 250° C., preferably 120 to 220° C., more preferably 130 to 210° C., most preferably 150 to 200° C. The preferred residence time at this temperature is preferably at least 10 minutes, more preferably at least 20 minutes, most preferably at least 30 minutes, and typically at most 60 minutes.

In a preferred embodiment of the present invention, the water-absorbing polymer particles are cooled after the surface crosslinking. The cooling is preferably performed in contact coolers, more preferably paddle coolers and most preferably disk coolers. Suitable coolers are, for example, Hosokawa Bepex® Horizontal Paddle Coolers (Hosokawa Micron GmbH; Leingarten; Germany), Hosokawa Bepex® Disc Coolers (Hosokawa Micron GmbH; Leingarten; Germany), Holo-Flite® coolers (Metso Minerals Industries Inc.; Danville; USA) and Nara Paddle Coolers (NARA Machinery Europe; Frechen; Germany). Moreover, fluidized bed coolers may also be used.

In the cooler, the water-absorbing polymer particles are cooled to 20 to 150° C., preferably 30 to 120° C., more preferably 40 to 100° C. and most preferably 50 to 80° C.

Subsequently, the surface crosslinked polymer particles can be classified again, with fines or coarse particles being removed and recycled into the process.

To further improve the properties, the surface crosslinked polymer particles can be coated or remoisturized.

The remoisturizing is preferably performed at 30 to 80° C., more preferably at 35 to 70° C., most preferably at 40 to 60° C. At excessively low temperatures, the water-absorbing polymer particles tend to form lumps, and, at higher temperatures, water already evaporates to a noticeable degree. The amount of water used for remoisturizing is preferably from 0.2 to 10% by weight, more preferably from 0.5 to 7.0% by weight and most preferably from 1.0 to 5% by weight. The remoisturizing increases the mechanical stability of the polymer particles and reduces their tendency to static charging. The remoisturizing is advantageously performed in the cooler after the thermal drying.

Suitable coatings for improving the free swell rate FSR and the permeability of the swollen gel bed SFC are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The present invention further provides water-absorbing polymer particles which are obtainable by the process according to the invention and are characterized by
a) a free swell rate FSR of at least 0.20 g/g·s,
b) a centrifuge retention capacity CRC of at least 26.0 g/g,
c) an absorption under a load of 49.2 g/cm² $AUL_{0.7psi}$ of at least 20.0 g/g,
d) a permeability of the swollen gel bed SFC of at least $85 \times 10^{-7}$ cm³ s/g and
e) a ratio of the permeability of the swollen gel bed SFC to the centrifuge retention capacity CRC of at most 3.7.

A favorable ratio of the permeability of the swollen gel bed SFC to centrifuge retention capacity CRC indicates that a sufficiently high CRC is achieved for a given SFC.

The inventive water-absorbing polymer particles have a free swell rate FSR of at least 0.20 g/g·s, preferably at least 0.30 g/g·s.

The inventive water-absorbing polymer particles have a ratio of the permeability of the swollen gel bed SFC to centrifuge retention capacity CRC of at most 3.7, preferably at most 3.5.

The inventive water-absorbing polymer particles have an absorption under a load of 49.2 g/cm² $AUL_{0.7psi}$, of typically at least 20.0 g/g, preferably at least 23.0 g/g.

The present invention further provides hygiene articles comprising inventive water-absorbing polymer particles.

The hygiene articles typically comprise a water-impervious backside, a water-pervious topside and an intermediate absorbent core composed of the inventive water-absorbing polymer particles and fibers, preferably cellulose. The proportion of the inventive water-absorbing polymer particles in the absorbent core is preferably 20 to 100% by weight and more preferably 50 to 100% by weight.

Analysis Methods:

The standard test methods described hereinafter and designated "WSP" are described in: "Standard Test Methods for the Nonwovens Industry", 2005 edition, published jointly by the Worldwide Strategic Partners EDANA (Avenue Eugène Plasky, 157, 1030 Brussels, Belgium, www.edana.org) and INDA (1100 Crescent Green, Suite 115, Cary, N.C. 27518, U.S.A., www.inda.org). This publication is available both from EDANA and from INDA.

The measurements should, unless stated otherwise, be conducted at an ambient temperature of 23±2° C. and a relative air humidity of 50±10%. The water-absorbing polymer particles are mixed thoroughly before the measurement.

Particle Size Distribution

The particle size distribution (PSD) is determined by EDANA (European Disposables and Nonwovens Association) recommended test method No. WSP 220.2-05 "Particle Size Distribution". In a departure from the test method, screens having the following hole sizes are used: 150, 200, 300, 500, 600 and 710 µm.

Residual Moisture Content

The residual moisture content (RMC, water content of the polymer) is determined by EDANA (European Disposables and Nonwovens Association) recommended test method No. 230.2-05 "Moisture Content".

Centrifuge Retention Capacity

The centrifuge retention capacity (CRC) is determined by EDANA recommended test method No. WSP 241.2-05 "Fluid Retention Capacity in Saline, After Centrifugation".

Extractable Polymers

The proportion of extractable polymers (extractables) is determined by EDANA recommended test method No. 270.2-05 "Extractables".

Absorption Under a Load of 49.2 g/Cm² ($AUL_{0.7psi}$)

The absorption under a load of 49.2 g/cm² ($AUL_{0.7psi}$) is determined analogously to EDANA recommended test method No. WSP 242.2-05 "Absorption Under Pressure, Gravimetric Determination", except that a load of 49.2 g/cm² ($AUL_{0.7psi}$) is established rather than a load of 21.1 g/cm² ($AUL_{0.3psi}$).

Free Swell Rate

To determine the free swell rate (FSR), 1.00 g ($=W_1$) of the water-absorbing polymer particles is weighed into a 25 ml beaker and distributed homogeneously over its base. Then 20 ml of a 0.9% by weight sodium chloride solution are metered into a second beaker by means of a dispenser and the contents of this beaker are added rapidly to the first and a stopwatch is started. As soon as the last drop of salt solution has been absorbed, which is recognized by the disappearance of the reflection on the liquid surface, the stopwatch is stopped. The exact amount of liquid which has been poured out of the second beaker and absorbed by the polymer in the first beaker is determined accurately by reweighing the second beaker ($=W_2$). The time interval required for the absorption, which has been measured with the stopwatch, is designated as t. The disappearance of the last liquid droplet on the surface is determined as the time t.

The free swell rate (FSR) is calculated therefrom as follows:

$$FSR[g/g\ s] = W_2/(W_1 \times t)$$

If the moisture content of the water-absorbing polymer particles, however, is more than 3% by weight, the weight $W_1$ should be corrected to take account of this moisture content.

$$W_{1,corrected} = W_{1,measured} \times (1-RF)$$

Saline Flow Conductivity

The saline flow conductivity (SFC) of a swollen gel layer under a pressure of 0.3 psi (2070 Pa) is determined, as described in EP 2 535 698 A1, with a weight of 1.5 g of water-absorbing polymer particles as a urine permeability measurement (UPM) of a swollen gel layer. The flow is detected automatically.

The saline flow conductivity (SFC) is calculated as follows:

$$SFC[cm^3 s/g] = (Fg(t=0) \times L_0)/(d \times A \times WP)$$

where $Fg(t=0)$ is the flow of NaCl solution in g/s, which is obtained using linear regression analysis of the $Fg(t)$ data of the flow determinations by extrapolation to $t=0$, $L_0$ is the thickness of the gel layer in cm, d is the density of the NaCl solution in $g/cm^3$, A is the area of the gel layer in $cm^2$, and WP is the hydrostatic pressure over the gel layer in $dynes/cm^2$.

EXAMPLES

Step 1
Production of the Polymer Gel

By continuously mixing water, 50% by weight sodium hydroxide solution and acrylic acid, a 42.7% by weight acrylic acid/sodium acrylate solution was prepared such that the degree of neutralization was 75.0 mol %. After the components had been mixed, the monomer solution was cooled continuously to a temperature of 30° C. by means of a heat exchanger and degassed with nitrogen. The polyethylenically unsaturated crosslinker used was 3-tuply ethoxylated glyceryl triacrylate (about 85% by weight purity). The amount used, based on the acrylic acid used (boaa), was 0.39% by weight. To initiate the free-radical polymerization, the following components were used: 0.002% by weight boaa of hydrogen peroxide, metered in as a 2.5% by weight aqueous solution, 0.1% by weight boaa of sodium peroxodisulfate, metered in as a 15% by weight aqueous solution, and 0.01% by weight boaa of ascorbic acid, metered in as a 0.5% by weight aqueous solution. The throughput of the monomer solution was 800 kg/h.

The individual components were metered continuously into a List ORP 250 Contikneter continuous kneader reactor (List AG, Arisdorf, Switzerland). In the first half of the reactor, 26.3 kg/h of removed fines having a particle size of less than 150 µm were additionally added, these having been obtained in the classification after grinding and drying of the polymer.

The reaction solution had a feed temperature of 30° C. The residence time of the reaction mixture in the reactor was about 15 minutes.

Extrusion

The polymer gel thus obtained was extruded with an ECT EXR T80 extruder (ECT GmbH, Mühlacker, Germany). The temperature of the polymer gel in the course of extrusion was 86° C. The extruder jacket was heated with oil at 150° C. The ratio of internal length to internal diameter of the extruder (L/D) was 4. The dies used were die plates having a thickness of 33 mm, a diameter of 90 mm and having holes having a diameter of 8 mm. As a result of the mechanical mounting of the die plate, only a diameter of 80 mm is utilizable for the extrusion. This gives rise to a maximum utilizable area of the die plate of 6400 $mm^2$. This area is equal to the exit area of the extruder shaft. The orifice ratios reported in table 1 were established by varying the number of holes. The specific mechanical energy (SME) of the extrusion in the experiments was 24 to 52 kWh/t.

The extrusion conditions, including the orifice ratio of the dies used in the examples and comparative examples, are reported in table 1.

Drying, grinding and classification of the polymer gel

The extruded polymer gel was distributed on drying sheets with a sieve base (mesh size 250 µm, wire diameter 130 µm), and dried in an air circulation drying cabinet at 175° C. for 70 min. The loading of the metal sheets with polymer gel was 0.81 $g/cm^2$.

The dried polymer gel was ground by means of a one-stage roll mill (three milling runs, 1st milling run with gap width 2000 µm, 2nd milling run with gap width 600 µm and 3rd milling run with gap width 400 µm).

The ground dried polymer gel was classified and a synthetic particle size distribution (PSD) was blended therefrom as follows:

| Screen fraction [µm] | Proportion by weight [%] |
|---|---|
| <150 | 0 |
| 150-200 | 5.0 |
| 200-300 | 13.8 |
| 300-500 | 42.7 |
| 500-600 | 27.9 |
| 600-710 | 10.6 |
| >710 | 0 |

A portion of the fines from the screening (sieve fraction having a particle size <150 µm) was used for metered addition into the reactor in the course of polymerization.

The base polymer thus obtained was analyzed for its centrifuge retention capacity (CRC) and the amount of extractable polymers after 16 h. CRC and extractables were corrected with respect to the residual moisture content, by always using the dry polymer mass in the calculations:

$$m_{dry} = m_{moist} \times (1-RMC)$$

The properties of the dried polymer gels are summarized in table 1. $\Delta p$ is the pressure differential between the pressure in the extruder upstream of the die plate and ambient pressure.

Surface Crosslinking of the Polymer Gel

For each surface crosslinking operation, 1200 g of the dried polymer with synthetic PSD were coated in an M5 Pflugschar® plowshare mixer with heating jacket (Gebr. Lödige Maschinenbau GmbH, Paderborn, Germany) at 23° C. and a shaft speed of 200 revolutions per minute by means of a two-phase spray nozzle with the following solution (based in each case on the base polymer):

0.994% by weight of isopropanol
0.14% by weight of a solution of 50% by weight of 1,3-propanediol and 50% by weight of N-(2-hydroxyethyl)-2-oxazolidinone
0.70% by weight of 1,2-propanediol
2.273% by weight of a 22% by weight aqueous aluminum lactate solution
0.004% by weight of sorbitan monolaurate (Span 20®, Croda International PLC)
0.431% by weight of water After the spray application, the product was withdrawn from the mixer and transferred into a second mixer of the same type, which had been preheated with heating fluid at 238° C. The shaft speed was set to 50 revolutions per minute and the product was brought to a product temperature of 185° C. In order to maintain this temperature, the temperature of the heating fluid was reduced appropriately. Starting from the 25th minute after introduction of polymer, samples each of about 20 g were withdrawn from the reaction mixture every 5 minutes. A total of 10 samples were taken. The product samples were screened off through a screen having a mesh size of 710 µm, in order to remove agglomerates. The SFC values of all the samples were determined. For the sake of comparability, the samples having SFC values closest to 100 $(cm^3 \cdot s)/10^7$ g were selected. Their properties are reported in table 2.

TABLE 1

Extrusion conditions and properties of dried polymer gels

| # | Extrusion | | | | Polymer | | |
|---|---|---|---|---|---|---|---|
| | Pressure [$bar_{abs}$] | Pressure differential Δp [bar] | Orifice ratio [%] | Throughput [kg/h] | CRC [g/g] | Extractables 16 h [% by wt.] | CRC/Extr. |
| Comp. 1 | 17 | 16 | 12 | 126 | 34.0 | 14.9 | 2.3 |
| Comp. 2 | 20 | 19 | 12 | 138 | 34.3 | 15.4 | 2.2 |
| Comp. 3 | 18 | 17 | 66 | 252 | 35.2 | 14.5 | 2.4 |
| Ex. 1 | 14 | 13 | 66 | 190 | 36.3 | 14.7 | 2.5 |
| Ex. 2 | 6 | 5 | 44 | 78 | 37.2 | 13.4 | 2.8 |

TABLE 2

Properties of the surface crosslinked polymers

| | SFC [$cm^3 \cdot s)/10^7$ g] | CRC [g/g] | $AUL_{0.7\,psi}$ [g/g] | SFC/CRC | FSR [g/gs] |
|---|---|---|---|---|---|
| Comp. 1 | 109 | 24.8 | 23.9 | 4.4 | 0.30 |
| Comp. 2 | 100 | 25.5 | 24.5 | 3.9 | 0.31 |
| Comp. 3 | 102 | 26.3 | 24.3 | 3.9 | 0.32 |
| Ex. 1 | 91 | 26.3 | 23.8 | 3.5 | 0.31 |
| Ex. 2 | 89 | 26.9 | 25.2 | 3.3 | 0.22 |

Table 1 shows that a pressure differential of 4 to less than 14 bar leads to polymer gels having a favorable ratio of centrifuge retention capacity CRC to extractable polymers Extr. Greater pressure differentials worsen the ratio.

Table 2 shows that, given a sufficiently high free swell rate FSR, a lower ratio of SFC/CRC than in the comparative examples can be achieved. Only the free swell rate FSR is significantly worse in example 2 compared to the comparative examples and example 1.

The invention claimed is:

1. A process for producing water-absorbing polymer particles, comprising
   a) a polymerization step in which an aqueous monomer solution comprising at least one ethylenically unsaturated monomer M which bears an acid group and optionally has been at least partly neutralized and at least one crosslinker are polymerized to obtain an aqueous polymer gel;
   b) a pelletization step in which the aqueous polymer gel having a solids content of 35 to 70% by weight and a temperature of 75 to 125° C. is forced from a high-pressure zone through a die plate into a low-pressure zone and pellets are obtained, the pressure differential between the high-pressure zone and the low-pressure zone being 4 to less than 14 bar and the orifice ratio of the die plate being 30 to 80%;
   c) a drying step in which the pellets are dried to a moisture content of less than 10% by weight;
   d) a grinding step and a classifying step to obtain water-absorbing polymer particles; and
   e) surface crosslinking of the water-absorbing polymer particles.

2. The process according to claim 1, wherein the monomer M is acrylic acid.

3. The process according to claim 1, wherein the monomer M has been neutralized to an extent of 25 to 85 mol %.

4. The process according to claim 1, wherein at least 0.25% by weight of the crosslinker, based on the unneutralized monomer M, is used in step a).

5. The process according to claim 1, wherein the monomer solution is polymerized in step a) in a polymerization reactor having at least two shafts that rotate in an axially parallel manner.

6. The process according to claim 1, wherein a thickness of the die plate in step b) is 15 to 45 mm.

7. The process according to, wherein a diameter of holes in the die plate in step b) is 2 to 20 mm.

8. The process according to claim 1, wherein the pelletization step b) is conducted in an extruder comprising an elongated extruder housing, an outlet orifice provided with the die plate, and at least one screw shaft which rotates within the extruder housing and which conveys the polymer gel in the direction of the outlet orifice while generating a backpressure.

9. The process according to claim 1, wherein the dried pellets have a ratio of centrifuge retention capacity CRC to the water-soluble components of at least 2.5.

10. Water-absorbing polymer particles obtained by a process according to claim 1, characterized by
   a) a free swell rate FSR of at least 0.20 g/g·s,
   b) a centrifuge retention capacity CRC of at least 26.0 g/g,
   c) an absorption under a load of 49.2 g/cm$^2$ $AUL_{0.7psi}$ of at least 20.0 g/g,
   d) a permeability of the swollen gel bed SFC of at least 85×10$^{-7}$ cm$^3$ s/g, and
   e) a ratio of the permeability of the swollen gel bed SFC to the centrifuge retention capacity CRC of at most 3.7.

11. A hygiene article comprising water-absorbing polymer particles obtained according to claim 1 and characterized by
   a) a free swell rate FSR of at least 0.20 g/g·s,
   b) a centrifuge retention capacity CRC of at least 26.0 g/g,
   c) an absorption under a load of 49.2 g/cm$^2$ AUL0.7 psi of at least 20.0 g/g,
   d) a permeability of the swollen gel bed SFC of at least 85×10−7 cm$^3$ s/g, and
   e) a ratio of the permeability of the swollen gel bed SFC to the centrifuge retention capacity CRC of at most 3.7.

* * * * *